(12) United States Patent
Berge et al.

(10) Patent No.: US 7,230,029 B2
(45) Date of Patent: Jun. 12, 2007

(54) FATTY ACID ANALOGUES FOR THE TREATMENT OF PROLIFERATIVE SKIN DISORDERS

(75) Inventors: Rolf Berge, Norway (NO); Karsten Kristiansen, Brody (DK)

(73) Assignee: Thia Medica AS, Bergen (NO)

(*) Notice: Subject to any disclaimer, the term of this patent is extended or adjusted under 35 U.S.C. 154(b) by 294 days.

(21) Appl. No.: 10/363,963

(22) PCT Filed: Sep. 27, 2001

(86) PCT No.: PCT/NO01/00393

§ 371 (c)(1),
(2), (4) Date: May 8, 2003

(87) PCT Pub. No.: WO02/26218

PCT Pub. Date: Apr. 4, 2002

(65) Prior Publication Data

US 2004/0019108 A1    Jan. 29, 2004

(30) Foreign Application Priority Data

Sep. 27, 2000   (NO) .................................. 20004844

(51) Int. Cl.
*A61K 31/20*   (2006.01)
*A61K 31/201*  (2006.01)
*A61K 31/22*   (2006.01)
*A61K 31/231*  (2006.01)

(52) U.S. Cl. ...................... 514/546; 514/549; 514/550; 514/557; 514/558; 514/560

(58) Field of Classification Search ................... 562/26; 514/546, 549, 550, 557, 558, 560
See application file for complete search history.

(56) References Cited

U.S. PATENT DOCUMENTS 6,511,670 B1 * 1/2003 Maignan et al. ............. 424/401

6,924,309 B2 * 8/2005 Ferrante et al. ............. 514/560

FOREIGN PATENT DOCUMENTS

| EP | 0273202 | * | 7/1988 |
| EP | 0742004 A | | 11/1996 |
| WO | WO 01/21575 A | | 3/2001 |
| WO | WO0168582 A | | 9/2001 |

* cited by examiner

*Primary Examiner*—Bernard Dentz
(74) *Attorney, Agent, or Firm*—Francis C. Hand; Carella, Byrne, Bain eta

(57) ABSTRACT

The present invention relates to fatty acid analogues of the general formula (I): $R_1\text{-}[x_i\text{-}CH_2]_n\text{—}COOR_2$ wherein $R_1$ is; a $C_1\text{--}C_{24}$ alkene with one or more double bonds and/or with one or more triple bonds, and/or a $C_1\text{--}C_{24}$ alkyne, and/or a $C_1\text{--}C_{24}$ alkyl, or a $C_1\text{--}C_{24}$ alkyl substituted in one or several positions with one or more compounds selected from the group comprising fluoride, chloride, hydroxy, $C_1\text{--}C_4$ alkoxy, $C_2\text{--}C_4$ alkylthio, $C_1\text{--}C_5$ acyloxy or $C_1\text{--}C_4$ alkyl, and wherein R2 represents hydrogen or $C_1\text{--}C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and with the proviso that if R1 is an alkyne or alkene, then the carbon-carbon triple bond or double bond is positioned between the ($\omega$-1) carbon and the ($\omega$-2) carbon, or between the ($\omega$-2) carbon and the ($\omega$-3) carbon, or between the ($\omega$-3) carbon and the ($\omega$-4) carbon, which can be used for the treatment and/or prevention of proliferative skin disorders. More specifically the invention relates to the inhibition of proliferation and/or differentiation of keratinocytes.

21 Claims, 3 Drawing Sheets

FATTY ACID ANALOGUES FOR THE TREATMENT OF PROLIFERATIVE SKIN DISORDERS

This application is a national stage entry of PCT/NO00393 filed Sep. 27, 2001.

The present invention relates to fatty acid analogues that can be used for the treatment and/or prevention of proliferative skin diseases. More specifically, the invention relates to the use of the fatty acid analogues for the treatment and/or prevention of diseases related to the regulation of keratinocyte differentiation and proliferation.

BACKGROUND OF THE INVENTION

Proliferative skin diseases are widespread throughout the world and afflict millions of humans and their domesticated animals. Proliferative skin diseases are characterized by keratinocyte cell proliferation, or division, and may also be associated with incomplete epidermal differentiation. Psoriasis is the most serious of the proliferative skin diseases with which this invention is concerned.

Psoriasis is a genetically determined disease of the skin characterized by two biological hallmarks. First, there is a profound epidermal hyperproliferation related to accelerated and incomplete differentiation. Second, there is a marked inflammation of both epidermis and dermis with an increased recruitment of T lymphocytes, and in some cases, formation of neutrophil microabcesses. Many pathologic features of psoriasis can be attributed to alterations in the growth and maturation of epidermal keratinocytes, with increased proliferation of epidermal cells, occurring within 0.2 mm of the skin's surface. Traditional investigations into the pathogenesis of psoriasis have focused on the increased proliferation and hyperplasia of the epidermis. In normal skin, the time for a cell to move from the basal layer through the granular layer is 4 to 5 weeks. In psoriatic lesions, the time is decreased sevenfold to tenfold because of a shortened cell cycle time, an increase in the absolute number of cells capable of proliferating, and an increased proportion of cells that are actually dividing. The hyperproliferative phenomenon is also expressed, although to a substantially smaller degree, in the clinically uninvolved skin of psoriatic patients.

A common form of psoriasis, psoriasis vulgaris, is characterized by well-demarcated erythematous plaques covered by thick, silvery scales. A characteristic finding is the isomorphic response (Koebner phenomenon), in which new psoriatic lesions arise at sites of cutaneous trauma. Lesions are often localized to the extensor surfaces of the extremities, and the nails and scalp are also commonly involved.

Therapeutic efforts in psoriasis are aimed at decreasing the proliferative rate of the epidermis, either by direct action on cell division or indirectly by reducing the immunological response. For patients with localized, limited psoriasis, administration of topical corticosteroids is the most convenient outpatient therapy. Rapid improvement may be seen with this approach, but the beneficial short-term efficacy is limited and chronic topical corticosteroid treatment is not advisable. Side effects from chronic topical corticosteroid therapy can include atrophy of the skin, development of tolerance to the agent used (tachyphylaxis), and serious exacerbation of the disease after discontinuation. Pituitary-adrenal suppression is a potential and serious complication of potent topical corticosteroid therapy, particularly when the agent covers a large portion of the body surface and is used under occlusive dressings.

The retinoids, particularly etretinate, either alone or in combination with PUVA, are also an effective treatment for psoriasis. Etretinate is especially useful in the exfoliative and pustular varieties of psoriasis. However, several major potential complications must be monitored in patients placed on retinoids. As a class, the retinoids are potent teratogens and should not be given to women of childbearing age who are not using adequate contraception. Etretinate, like other retinoids, can produce elevations in cholesterol and triglyceride levels; therefore dietary regulation may be necessary. In addition, because etretinate can induce hepatotoxicity, liver function tests should be performed before and at regular intervals during use of the drug.

Considering the complications and side effects attendant to the use of different drugs and photochemotherapy currently used in treating a skin proliferative disease such as psoriasis, there is a need for a new method and a new composition to inhibit keratinocyte proliferation to alleviate the symptoms of skin proliferation diseases.

DETAILED DESCRIPTION OF THE INVENTION

The epidermis is a stratified squamous epithelium in which the basal layer is composed of progenitor cells that undergo a highly sequentially differentiation program as they migrate through the suprabasal layers. Each step of differentiation is characterized by the expression of specific marker genes. The proliferating basal cells express keratin genes such as K5 and K14, whereas the transition of basal cells from basal layer to spinous layer is associated with upregulation of the early differentiation markers keratin 1 (K1) and keratin 10 (K10). The transition from the spinous to the granular layer is accompanied by upregulation of genes encoding structural proteins of the cornified envelope such as involucrin (IVL) and later transglutaminase (TGM1).

The epidermis represents a tissue with high rates of fatty acid and cholesterol metabolism where accumulation and deposition of cholesterol, fatty acids and sphingolipids constitute an integral part of the terminal epidermal differentiation program culminating in the formation of a competent epidermal barrier.

It is speculated that the PPAR family plays a role in the differentiation of keratinocytes, and in the present study we have compared the effect of known PPAR ligands with the effect obtained with TTA, a compound of the present invention.

In the present study we have in detail analyzed the expression of the PPARs during ex vivo differentiation of human keratinocytes, in isolated basal and suprabasal cells, and in sections of human skin. Using concentrations of PPAR subtype selective ligands that exclusively targeted the appropriate PPAR subtype we have found that PPARα and PPARγ selective ligands have negligible effect on keratinocyte marker gene expression (data not shown). Interestingly, the PPARδ selective ligand L165041 induced in a dose-dependent manner expression of involucrin. All three PPAR subtype selective ligands either alone or in combination only modestly effected keratinocyte proliferation.

However, the present patent application discloses that a compound of the invention, i.e the thia-substituted fatty acid tetradecylthioacetic acid (TTA), strongly induced expression of keratinocyte differentiation marker genes and exerted a profound antiproliferative action on said keratinocytes.

TTA may thus hold promises as an interesting compound for the treatment of various epidermal disorders characterized by aberrant differentiation.

The present invention consequently discloses that modified fatty acid analogues at non-cytotoxic concentrations can be used for the treatment and/or prevention of proliferative skin disorders.

The present invention relates to the use of fatty acid analogues of the general formula (I):

(I)

wherein $R_1$ is;
- a $C_1$–$C_{24}$ alkene with one or more double bonds and/or with one or more triple bonds, and/or
- a $C_1$–$C_{24}$ alkyne, and/or
- a $C_1$–$C_{24}$ alkyl, or a $C_1$–$C_{24}$ alkyl substituted in one or several positions with one or more compounds selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and with the proviso that if R1 is an alkyne or alkene, then the carbon-carbon triple bond or double bond is positioned between the (ω-1) carbon and the (ω-2) carbon, or between the (ω-2) carbon and the (ω-3) carbon, or between the (ω-3) carbon and the (ω-4) carbon, or a salt, prodrug or complex thereof, for the preparation of a pharmaceutical composition for the treatment and/or prevention of proliferative skin disorders.

The term "prodrug" is defined in the industry standard: "The Concise Chemical and Technical Dictionary", 4$^{th}$ edition (1986), by Bennett, printed by Edward Arnold (Australia) Pty Ltd., as "Biologically inactive compound broken down in the body to release medication".

More specifically, the invention relates to the use of the compounds for the regulation of differentiation and proliferation of keratinocytes.

Presently preferred embodiments of the present invention relates to the compounds tetradecylthioacetic acid (TTA) and tetradecylselenoacetic acid (TSA).

A further aspect of the invention relates to a method for the treatment and/or inhibition of proliferative skin diseases, said method comprising the step of administering to a mammal in need thereof an effective amount of fatty acid analogues of the general formula (I):

(I)

wherein $R_1$ is;
- a $C_1$–$C_{24}$ alkene with one or more double bonds and/or with one or more triple bonds, and/or
- a $C_1$–$C_{24}$ alkyne, and/or
- a $C_1$–$C_{24}$ alkyl, or a $C_1$–$C_{24}$ alkyl substituted in one or several positions with one or more compounds selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and with the proviso that if R1 is an alkyne or alkene, then the carbon-carbon triple bond or double bond is positioned between the (ω-1) carbon and the (ω-2) carbon, or between the (ω-2) carbon and the (ω-3) carbon, or between the (ω-3) carbon and the (ω-4) carbon, or a salt, prodrug or complex thereof.

A preferable embodiment of invention comprising topically administering to a mammal in need of such treatment a therapeutically effective concentration of a compound of the present invention.

FIGURE LEGENDS

ADMINISTRATION OF THE COMPOUNDS OF THE PRESENT INVENTION

Figure 1:
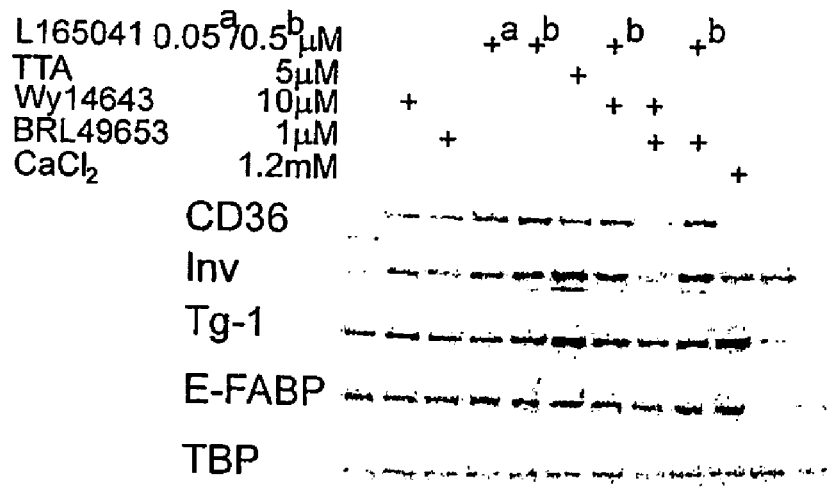
FIG. 1 shows the induction of epidermal differentiation specific genes and CD36.
Figure 1:
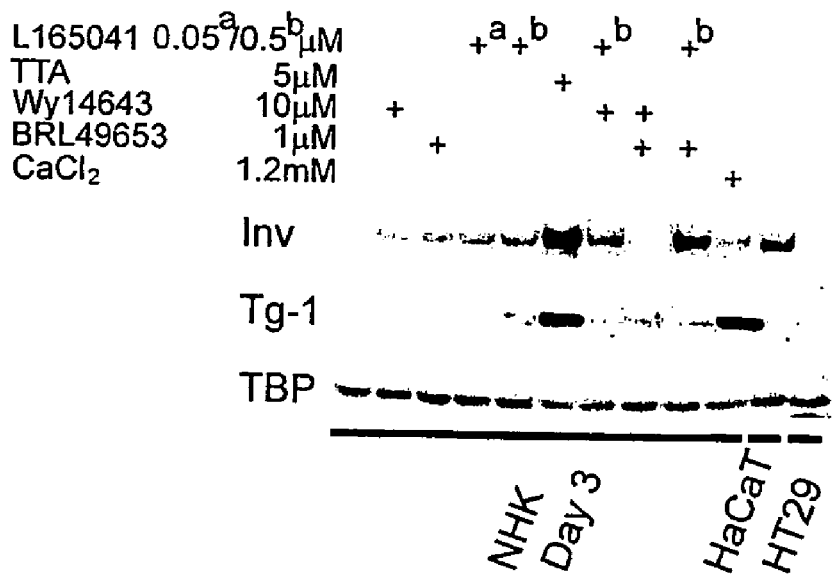

As a pharmaceutical medicament the compounds of the present invention may be administered directly to the mammal by any suitable technique, including parenterally, intranasally, orally, or by absorption through the skin. They can be administered locally or systemically. The specific route of administration of each agent will depend, e.g., on the medical history of the mammal.

Preferably the compounds of the present invention are administered topically.

The compounds of the present invention may be administered in dispersions prepared in creams, ointments, oil or other suitable carrier and/or diluent such as glycerol, liquid polyethylene glycols and/or mixtures thereof.

The pharmaceutical forms suitable for topical use include sterile aqueous solutions (where water soluble) or dispersions and powders for the extemporaneous preparation of topical solutions or dispersion. In all cases, the form is preferably sterile although this is not an absolute requirement and is stable under the conditions of manufacture and storage. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganism can be brought about by various antibacterial and antifungal agents, for example, parabens, chlorobutanol, phenol, sorbic acid, thirmerosal and the like. In many cases, it will be preferable to include isotonic agents, for example, sugars or sodium chloride.

Topical solutions are prepared by incorporating the compounds of the present invention in the required amount in the appropriate solvent with various of the other ingredients enumerated above, as required, followed by where necessary filter sterilization.

As used herein "pharmaceutically acceptable carriers and/or diluents" include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the pharmaceutical compositions is contemplated.

In addition, the compounds of the present invention are appropriately administered in combination with other treatments for combating or preventing proliferative skin disorders.

The invention will be more fully understood by reference to the following examples. They should not, however, be construed as limiting the scope of the invention.

EXPERIMENTAL SECTION

EXAMPLE 1

Preparation and Characterisation of the Compounds

The Synthesis of 3-substituted Fatty Acid Analogues

The compounds used according to the present invention wherein the substituent $X_{i=3}$ is a sulphur atom or selenium atom may be prepared according to the following general procedure:

X Is a Sulphur Atom:

The thio-substituted compound used according to the present invention may be prepared by the general procedure indicated below:

The sulphur-compound, namely, tetradecylthioaceticacid (TTA), $(CH_3-(CH_2)_{13}-S-CH_2-COOH$ was prepared as shown in EP-345.038.

X Is a Selenium Atom:

the seleno-substituted compound used according to the present invention may be prepared by the following general procedure

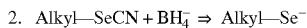
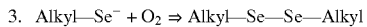

1. Alkyl-Hal+KSeCN Alkyl-SeCN . . .
2. Alkyl-SeCN+BH$_4^-$ Alkyl-Se$^-$
3. Alkyl-Se$^-$+O$_2$ Alkyl-Se—Se-Alkyl This compound was purified by carefully crystallisation from ethanol or methanol.

5.  Alkyl-Se$^-$+Hal-CH$_2$—COOH   Alkyl-Se—CH$_2$—COOH

The final compound, e.g. when alkyl is tetradecyl, $(CH_3-(CH_2)_{13}-Se-CH_2-COOH$ (tetradecylselinoacetic acid (TSA)) can be purified by crystallisation from diethyl ether and hexane.

Other compounds in accordance with the present invention can be synthesised as indicated in applicant's patent applications PCT/NO99/00135 (now U.S. Pat. No. 6,441,036) and NO 20001123.

EXAMPLE 2

The Effect of TTA on the Differentiation and Proliferation of Keratinocytes.

Materials and Methods

Cell Culture and Differentiation

Normal adult human epidermal keratinocytes were isolated from human skin obtained after plastic surgery. First passage keratinocytes were grown in serum-free KGM (GIBCO BRL/Life Technologies, Inc.) and replated in 75 cm$^2$ culture flask or in 96-well microtiterplates preheated at 37° C. at a density of 3500 cells/well. Cells were incubated in a humidified atmosphere of 5% CO$_2$ at 37° C. When cells reached 40% confluence they were treated with growth medium containing selective PPAR ligands (either alone or in combinations as indicated), tetradecylthioacetic acid (TTA) or 1,2 mM Ca$^{2+}$. Wy14643 was obtained from Calbiochem, BRL49653 was kindly provided by J. Fleckner, Novo Nordisk), L165041 was kindly provided by D. E. Moller (Merck Research Laboratories, Rahway, N.J.). TTA was manufactured in accordance with example 1. Medium was changed every day. For differentiation, keratinocytes at 40% confluence (day 0) were treated with 1,2 mM CaCl$_2$. Medium was changed every other day. HaCaT cells were obtained from L. Aarenstrup (Danish Cancer Society, Denmark). HaCaT cells were cultured in Dulbecco's modified Eagle's Medium (DMEM) with 10% fetal calf serum (FCS) and antibiotics (100 u/ml penicillin, 1 mg/ml streptomycin sulphate) in a humidified atmosphere of 5% CO$_2$ at 37° C. Medium was changed every other day.

Separation of Keratinocytes into Basal and Suprabasal Cells

Normal adult skin specimens obtained from plastic surgery were cleaned from fat and cut through the epidermal side using a scapula. The tissue was incubated over night on ice in 25 U/ml dispase II (Roche) made up in Hanks Buffered Saline Solution. The epidermis was peeled off using a pincer and the epidermal sheets were incubated in 0.05 mg/ml trypsin (1:250, GIBCO BRL/Life Technologies, Inc) at 37° C. until single cells were released. Trypsin activity was inhibited by the addition of serum-containing medium. The cells were centrifuged at 800 rcf and resuspended in prewarmed Keratinocyte-SFM (GIBCO BRL/Life Technologies, Inc). The cell suspension was added to tissue culture flasks coated with rat tail collagen. After 1 hour the non-attached cells were collected as the suprabasal fraction and the attaching basal cells were collected using a rubber policeman. Cell pellets were frozen at −70° C. until use.

Determination of Viability and Proliferation

Viability/proliferation was measured by a modification of the MTT assay introduced by Mosmann T (J Immunol Methods 65:55–63, 1983). Twenty-five μl of 5 mg/ml MTT in Ca$^{2+}$ and Mg$^{2+}$ free PBS (NaCl 8 g/l, KCl 0.2 g/l, Na$_2$HPO$_4$·2H$_2$O 1.44 g/l, KH$_2$PO$_4$0.2 g/l, pH 7.4) were added to each well, and plates were placed in an incubator until the growing crystals penetrated the cell walls, typically after three to four hours. Plates were flicked to remove medium and freeze thawed twice before formazan crystals were solubilized in ethanol:acetone. (60:40 w/w) by gentle shaking for 30 minutes at 40° C. The amount of formazan was quantified in an ELISA-reader at 540 nm. Background values at 650 nm were subtracted.

Determination of Tg-1 Expression by ELISA

Cells were subjected to two freeze-thaw cycles and transglutaminase type 1 (Tg-1) was determined by ELISA. Each well was blocked with 200 μl 1% BSA in PBS for one hour at 37° C. and then incubated for one hour at 37° C. with 100 μl Tg-1-specific monoclonal antibody B.C1 (Biomedical Technologies Inc) diluted 1:1000 in PBS-1% BSA. Wells were washed three times for 5 minutes in PBS-0.05% Tween 20 and incubated for one hour with 100 μl secondary horseradish peroxidase conjugated goat-anti-mouse antibody diluted 1:2500 in PBS-1% BSA. The wells were washed three times with PBS-0.05% Tween 20 and once with PBS. 100 μl o-phenylenediamine (OPD) substrate were added and after 30 minutes in the dark, reactions were stopped with 100 μl 2 N sulfuric acid. The amount of transglutaminase was measured by quantifying the OPD reaction with an ELISA-reader at 490 nm and subtracting background at 650 nm. In order to correct for variations in cell number all values were normalized to cell number.

Results

Effect on CD36

To evaluate how TTA and the various PPAR activators affected expression of a known PPAR responsive gene and differentiation of keratinocytes, we first measured the mRNA levels of CD36/FAT and the two differentiation markers, Inv and Tg-1 in NHK treated with PPAR selective activators and TTA over a period of three days (FIG. 1a). The proximal promoter of the CD36/FAT gene has been shown to harbor a PPAR responsive element. Administration of BRL49653 (PPARγ-ligand) or Wy14643 (PPARα-ligand) induced expression of CD36/FAT, and the PPARδ selective ligand L165041 induced a significant dose-dependent expression of CD36 suggesting that CD36/FAT is also PPARδ responsive gene.

Finally, addition of a compound of the present invention, i.e. TTA, induced expression of CD36/FAT mRNA to a level slightly higher than those observed with Wy14643 or BRL49653.

Treatment with $CaCl_2$, a well-established and potent inducer of keratinocyte differentiation did not induce expression of CD36/FAT.

Expression of Inv mRNA

As shown in FIG. 1a, treatment with Wy14643 resulted in a modest induction of Inv mRNA expression. Interestingly, addition of L165041 led to a dose-dependent induction of Inv mRNA expression, whereas BRL49653 alone had no effect on Inv mRNA expression. Simultaneous addition of L165041 and Wy14643 did not significantly increase the level of Inv mRNA expression. Similarly, combined treatment with Wy14643 and BRL49653 did not induce Inv mRNA expression above that observed with Wy14643 alone. Noteworthy, simultaneous addition of L165041 and BRL49653 strongly induced Inv mRNA expression indicating synergy between PPARδ and PPARγ. Western blotting essentially recapitulated the results obtained by RT-PCR showing a dose-dependent induction of Inv protein by L165041 and a strong synergy between L165041 and BRL49653 (FIG. 1b). Each PPAR-selective ligand induced expression of Tg-1 mRNA expression, and combinations of the PPAR selective ligands induced expression in an additive manner.

Addition of a compound of the present invention, i.e. TTA, induced expression of Inv and Tg-1 mRNA to levels that significantly exceeded those obtained by treatment with the PPAR selective ligands. The potency of TTA as an inducer of Inv and Tg-1 expression was even more conspicuous when expression was analyzed at the protein level by Western blotting (FIG. 1b). It should be noted that TTA induced Inv and Tg-1 mRNA and protein expression to levels equal to or higher than those observed upon treatment with $CaCl_2$. Taken together these results suggest that TTA apart from possibly inducing Inv and Tg-1 expression via PPAR-dependent pathways exerted a pronounced effect on Inv and Tg-1 expression by mechanisms unrelated to the function of TTA as a PPAR ligand and activator.

Figure 2:
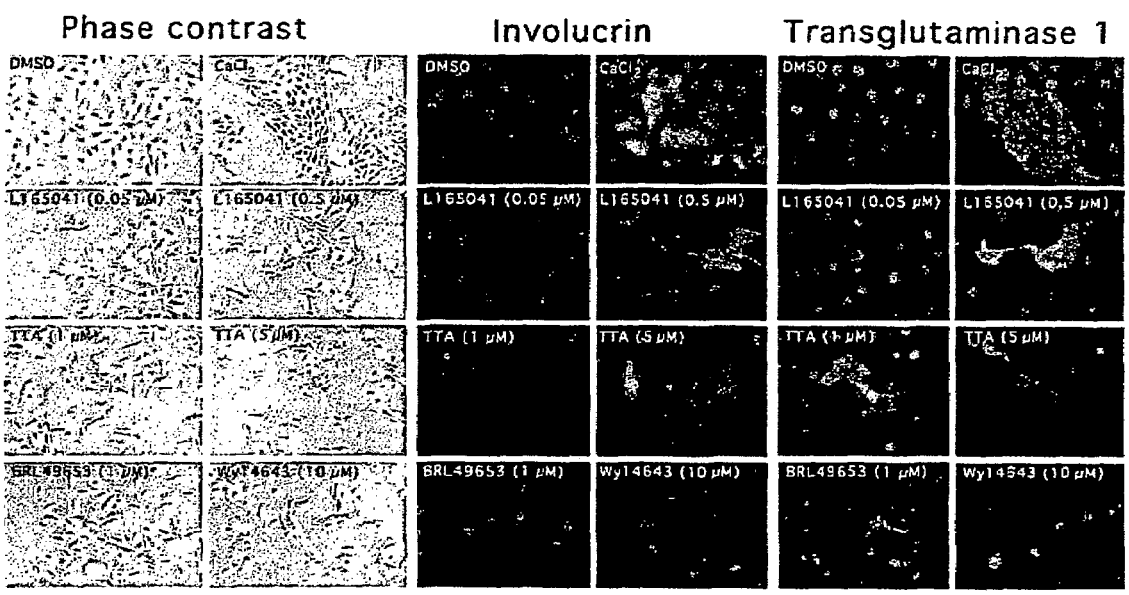
FIG. 2 shows the morphology and expression of differentiation specific genes of keratinocytes treated with TTA and selective PPAR ligands.
Figure 3:
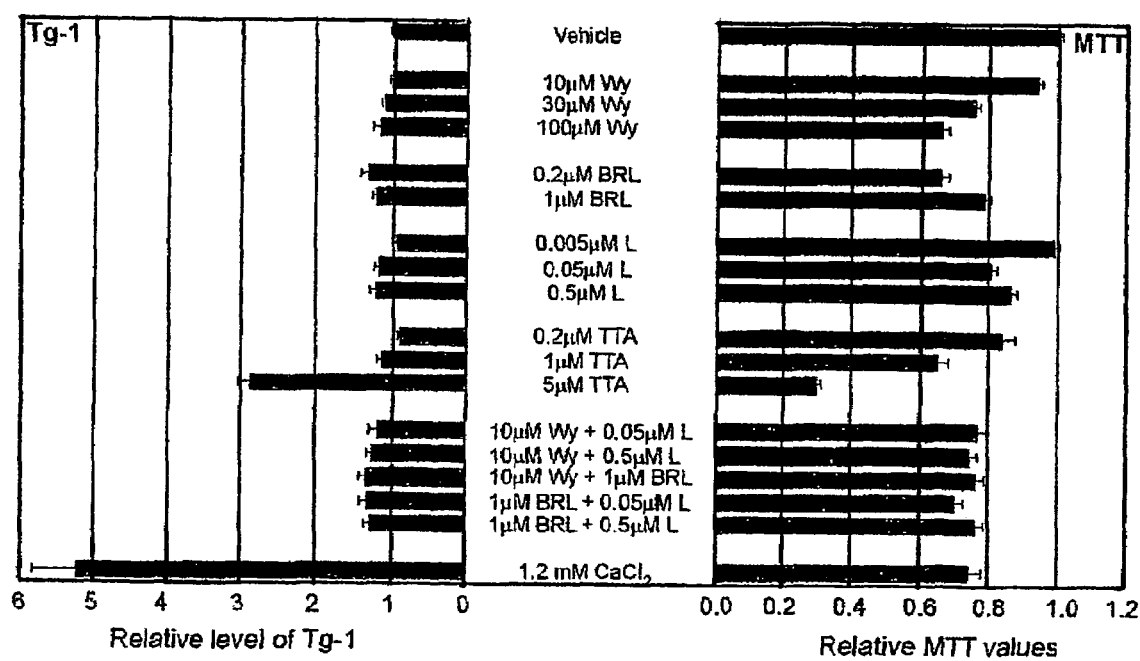
FIG. 3 shows that TTA induces the late epidermal differentiation marker Tg-1 and inhibits proliferation of keratinocytes.

Since TTA upregulated expression of keratinocyte differentiation markers, we examined whether treatment with TTA or the different subtype-selective PPAR activators, either alone or in combination affected NHK morphology during the early period of the differentiation process (FIG. 2). In addition, expression of Inv and Tg-1 was examined by indirect immunofluorescence microscopy (FIG. 3). As evaluated by phase contrast microscopy, the morphology of NHKs treated for three days with ligands or 1,2 mM $CaCl_2$ did not differ markedly. However, the density of cells in dishes treated with TTA was much lower than vehicle treated cells or cells treated with PPAR-selective ligands indicating that TTA apart from inducing keratinocyte specific markers also led to growth arrest or a decrease in the rate of proliferation.

Corroborating the results obtained by Western blotting, indirect immunofluorescence microscopy revealed comparable levels of expression of Inv and Tg-1 in the $CaCl_2$- and TTA-treated cells. Furthermore, this analysis also showed that the PPARδ selective ligand L165041 in a dose-dependent manner induced Inv expression.

Differentiation of keratinocytes is correlated with an increase in cell size. Of interest, careful comparison of the morphology of $CaCl_2$ and TTA treated cells indicated that the cytoplasmic to nuclear ratio of the TTA-treated cells tended to be smaller than that of $CaCl_2$-treated cells. Thus, even though treatment with $CaCl_2$ and TTA induced overlapping sets of keratinocyte marker genes, this observation suggests that TTA and $CaCl_2$ exert differential effects on keratinocyte differentiation. To examine in a more quantitative manner the effect of PPAR selective ligands and TTA on keratinocyte proliferation, NHK cells were treated with PPAR ligands, TTA and $CaCl_2$ as indicated in FIG. 3, and proliferation was assessed using a modification of the MTT assay as described in the Materials and Methods section. In parallel the expression of Tg-1 was monitored using an ELISA-based assay (FIG. 3b).

Noteworthy, TTA exerted a strong and dose-dependent inhibition of NHK cell proliferation that by far exceeded those observed for the PPAR selective ligands. The antiproliferative action of $CaCl_2$ was only marginal in these experiments. Recapitulating the results obtained by RT-PCR and Western blotting, only TTA and $CaCl_2$ significantly induced Tg-1 expression. Thus, the results obtained using the MTT assay clearly distinguished TTA from PPAR-selective ligands, and substantiated the notion that TTA strongly inhibited NHK cell proliferation and potently induced expression of keratinocyte differentiation marker genes.

The effect of treatment of a host with skin proliferation disease with a compound of the present invention can be evaluated by objective criteria such as an improvement of desquamation and erythema, reduction of the size of lesions as well as subjective criteria such as cessation of itching. Objective methods that are employed for establishing the effect of treatment of psoriasis patients include the resolution of plaques by visual monitoring and with photography.

The invention claimed is:

1. A method of treating a proliferative skin disorder comprising the administration of a pharmaceutical composition containing a fatty acid analogue having the following formula $$R_1\text{-}[x_i\text{-}CH_2]_n\text{—COOR}_2$$

wherein $R_1$ is;

a $C_2$–$C_{24}$ alkene with one or more double bonds and/or with one or more triple bonds, with the proviso that when n is 1 and $X_i$ is S, SO or $SO_2$ then $R_1$ cannot contain the C≡C—$CH_2$ moiety attaching to said $X_i$ atom, and/or a $C_2$–$C_{24}$ alkyne, and/or a $C_1$–$C_{24}$ alkyl, or a $C_1$–$C_{24}$ alkyl substituted in one or several positions with one or more moieties selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and with the proviso that if R1 is an alkyne or alkene, then the carbon-carbon triple bond or double bond is positioned between the (ω-1) carbon and the (ω-2) carbon, or between the (ω-2) carbon and the (ω-3) carbon, or between the (ω-3) carbon and the (ω-4) carbon, or a salt, prodrug or complex thereof, in an amount and for a period of time sufficient to treat said skin disorder.

2. A method as set forth in claim 1 wherein the skin proliferation disease is selected from the group comprising psoriasis, atopic dermatitis, non-specific dermatitis, primary irritant contact dermatitis, allergic contact dermatitis, lamellar ichthyosis, epidermolytic hyperkeratosis, pre-malignant sun induced keratosis, and seborrheic.

3. A method as set forth in claim 1 wherein the skin proliferation disease is psoriasis.

4. A method as set forth in claim 1 wherein $R_1$ is an alkene.

5. A method to inhibit a proliferative skin disorder comprising the administration of a pharmaceutical composition containing a fatty acid analogue having the following formula $$R_1\text{-}[x_i\text{-}CH_2]_n\text{—COOR}_2$$

wherein $R_1$ is;

a $C_2$–$C_{24}$ alkene with one or more double bonds and/or with one or more triple bonds, with the proviso that when n is 1 and $X_i$ is S, SO or $SO_2$ then $R_1$ cannot contain the C≡C—$_2$ moiety attaching to said $X_i$ atom, and/or a $C_2$–$C_{24}$ alkyne, and/or a $C_1$–$C_{24}$ alkyl, or a $C_1$–$C_{24}$ alkyl substituted in one or several positions with one or more moieties selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and with the proviso that if R1 is an alkyne or alkene, then the carbon-carbon triple bond or double bond is positioned between the (ω-1) carbon and the (ω-2) carbon, or between the (ω-2) carbon and the (ω-3) carbon, or between the (ω-3) carbon and the (ω-4) carbon, or a salt, prodrug or complex thereof, in an amount and for a period of time sufficient to inhibit said skin disorder.

6. A method as set forth in claim 5 wherein the skin proliferation disease is selected from the group comprising psoriasis, atopic dermatitis, non-specific dermatitis, primary irritant contact dermatitis, allergic contact dermatitis, lamellar ichthyosis, epidermolytic hyperkeratosis, pre-malignant sun induced keratosis, and seborrheic.

7. A method as set forth in claim 5 wherein the skin proliferation disease is psoriasis.

8. A method as set forth in claim 5 wherein $R_1$ is an alkene.

9. A method of inhibiting the proliferation and/or induction of differentiation of keratinocytes comprising the administration to a mammal in need thereof of a pharmaceutical composition containing a fatty acid analogue having the following formula $$R_1\text{-}[x_i\text{-}CH_2]_n\text{—COOR}_2$$

wherein $R_1$ is;

a $C_2$–$C_{24}$ alkene with one or more double bonds and/or with one or more triple bonds, with the proviso that when n is 1 and $X_i$ is S, SO or $SO_2$ then $R_1$ cannot contain the C≡C—$CH_2$ moiety attaching to said $X_i$ atom, and/or a $C_2$–$C_{24}$ alkyne, and/or a $C_1$–$C_{24}$ alkyl, or a $C_1$–$C_{24}$ alkyl substituted in one or several positions with one or more moieties selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and with the proviso that if R1 is an alkyne or alkene, then the carbon-carbon triple bond or double bond is positioned between the (ω-1) carbon and the (ω-2) carbon, or between the (ω-2) carbon and the (ω-3) carbon, or between the (ω-3) carbon and the (ω-4) carbon, or a salt, prodrug or complex thereof, in an amount and for a period of time sufficient to inhibit proliferation and/or induction of differentiation of keratinocytes.

10. A method as set forth in claim 9 wherein the skin proliferation disease is selected from the group comprising psoriasis, atopic dermatitis, non-specific dermatitis, primary irritant contact dermatitis, allergic contact dermatitis, lamellar ichthyosis, epidermolytic hyperkeratosis, pre-malignant sun induced keratosis, and seborrheic.

11. A method as set forth in claim 9 wherein the skin proliferation disease is psoriasis.

12. A method as set forth in claim 9 wherein $R_1$ is an alkene.

13. A method of treating a proliferative skin disorder comprising the administration of a pharmaceutical composition containing a fatty acid analogue having the following formula $$R_1\text{-}[x_i\text{-}CH_2]_n\text{---}COOR_2$$

wherein $R_1$ is;

a $C_1$–$C_{24}$ alkyl, or a $C_1$–$C_{24}$ alkyl substituted in one or several positions with one or more moieties selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and or a salt, prodrug or complex thereof, in an amount and for a period of time sufficient to treat said skin disorder.

14. A method of treating a proliferative skin disorder comprising the administration of a pharmaceutical composition containing the fatty acid analogue tetradecylthioacetic acid or a salt, prodrug or complex thereof, in an amount and for a period of time sufficient to treat said skin disorder.

15. A method of treating a proliferative skin disorder comprising the administration of a pharmaceutical composition containing the fatty acid analogue tetradecylselenoacetic acid or a salt, prodrug or complex thereof, in an amount and for a period of time sufficient to treat said skin disorder.

16. A method to inhibit a proliferative skin disorder comprising the administration of a pharmaceutical composition containing a fatty acid analogue having the following formula $$R_1\text{-}[x_i\text{-}CH_2]_n\text{---}COOR_2$$

wherein $R_1$ is;

a $C_1$–$C_{24}$ alkyl, or a $C_1$–$C_{24}$ alkyl substituted in one or several positions with one or more moieties selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and or a salt, prodrug or complex thereof, in an amount and for a period of time sufficient to inhibit said skin disorder.

17. A method to inhibit a proliferative skin disorder comprising the administration of a pharmaceutical composition containing the fatty acid analogue tetradecylthioacetic acid or a salt, prodrug or complex thereof, in an amount and for a period of time sufficient to inhibit said skin disorder.

18. A method to inhibit a proliferative skin disorder comprising the administration of a pharmaceutical composition containing the fatty acid analogue tetradecylselenoacetic acid or a salt, prodrug or complex thereof, in an amount and for a period of time sufficient to inhibit said skin disorder.

19. A method of inhibiting the proliferation and/or induction of differentiation of keratinocytes comprising the administration to a mammal in need thereof of a pharmaceutical composition containing a fatty acid analogue having the following formula $$R_1\text{-}[x_i\text{-}CH_2]_n\text{---}COOR_2$$

wherein $R_1$ is;

a $C_1$–$C_{24}$ alkyl, or a $C_1$–$C_{24}$ alkyl substituted in one or several positions with one or more moieties selected from the group comprising fluoride, chloride, hydroxy, $C_1$–$C_4$ alkoxy, $C_1$–$C_4$ alkylthio, $C_2$–$C_5$ acyloxy or $C_1$–$C_4$ alkyl, and wherein R2 represents hydrogen or $C_1$–$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and or a salt, prodrug or complex thereof, in an amount and for a period of time sufficient to inhibit proliferation and/or induction of differentiation of keratinocytes.

20. A method of inhibiting the proliferation and/or induction of differentiation of keratinocytes comprising the administration to a mammal in need thereof of a pharmaceutical composition containing the fatty acid analogue tetradecylthioacetic acid or a salt, prodrug or complex thereof, in an amount and for a period of time sufficient to inhibit proliferation and/or induction of differentiation of keratinocytes.

21. A method of inhibiting the proliferation and/or induction of differentiation of keratinocytes comprising the administration to a mammal in need thereof of a pharmaceutical composition containing the fatty acid analogue tetradecylselenoacetic acid or a salt, prodrug or complex thereof, in an amount and for a period of time sufficient to inhibit proliferation and/or induction of differentiation of keratinocytes.

* * * * *

UNITED STATES PATENT AND TRADEMARK OFFICE
CERTIFICATE OF CORRECTION

| | |
|---|---|
| PATENT NO. | : 7,230,029 B2 |
| APPLICATION NO. | : 10/363963 |
| DATED | : June 12, 2007 |
| INVENTOR(S) | : Rolf Berge et al. |

It is certified that error appears in the above-identified patent and that said Letters Patent is hereby corrected as shown below:

<u>Column 6</u>
Lines 1-2, cancel "5. … COOH"

<u>Column 9</u>
Line 63, change "$C_{-2}$ moiety" to -- $C\text{–}CH_2$ moiety--

Signed and Sealed this

Seventh Day of August, 2007

JON W. DUDAS
*Director of the United States Patent and Trademark Office*